United States Patent [19]
Castillo et al.

[11] Patent Number: 6,019,946
[45] Date of Patent: Feb. 1, 2000

[54] CATALYTIC STRUCTURE

[75] Inventors: Imelda L. Castillo, Somerset; Gerald S. Koermer, Roseland; Edward Balko, Middletown, all of N.J.

[73] Assignee: Engelhard Corporation, Iselin, N.J.

[21] Appl. No.: 08/970,944

[22] Filed: Nov. 14, 1997

[51] Int. Cl.[7] .............................. G01N 27/16; B01J 15/00; B01J 23/42

[52] U.S. Cl. ............................ 422/94; 422/98; 502/154; 502/339

[58] Field of Search .................................. 422/88, 90, 94, 422/95, 98; 502/152, 154, 326, 339

[56] References Cited

FOREIGN PATENT DOCUMENTS

| | | | |
|---|---|---|---|
| 0 551 519 A1 | 7/1993 | European Pat. Off. | ......... B01J 33/00 |
| 0 605 142 A1 | 7/1994 | European Pat. Off. | ......... B01J 23/02 |
| 37 23 052 A1 | 1/1989 | Germany | ........................ C23C 24/00 |
| 40 37 528 A1 | 5/1992 | Germany | ..................... G01N 27/407 |
| 2 134 413 | 8/1984 | United Kingdom | ............. B05D 3/02 |
| WO 98/22215 | 5/1998 | WIPO | .............................. B01J 37/02 |

*Primary Examiner*—Jill Warden

[57] ABSTRACT

A catalytic structure may be in the form of a ceramic support member having disposed on it a catalytic material which is a fired coating (124a-1, 124a-2) of a catalytic ink. The catalytic ink contains a liquid vehicle, at least one metal resinate compound and fine particles of a refractory metal oxide having dispersed thereon a catalytically effective amount of a catalytic metal component such as platinum or palladium or combinations of two or more catalytic metal components. The resulting catalytic structure may be employed as a catalytic gas sensor (24, 124) and further may include at least one conductor member (130, 132) which provides both temperature sensing of the fired catalytic coating (124a-1, 124a-2) to ascertain the degree of reaction taking place at the surface thereof, and heating of the support member to heat the fired catalytic coating to a temperature high enough to promote the catalytic reaction. The catalytic structure may be prepared by applying to a substrate a coating of a catalytic ink or paste and firing the applied coating.

25 Claims, 8 Drawing Sheets

CATALYTIC STRUCTURE

CROSS-REFERENCED TO RELATED APPLICATIONS

The present invention is also related to U.S. patent applications: EXHAUST GAS SENSOR (Docket No. 300.002); GAS SENSOR HAVING A POROUS DIFFUSION BARRIER LAYER AND METHOD OF MAKING SAME (Docket No. 300.003); and EXHAUST GAS SENSOR WITH FLOW CONTROL WITHOUT A DIFFUSION BARRIER (Docket No. 300.004), each application being filed of even date herewith and the disclosures of which are hereby expressly incorporated herein by reference.

BACKGROUND OF THE INVENTION

1. Field of the Invention

The present invention is concerned with catalytic structures comprising a fired coating of a catalytic ink adhered to a support member, such as a ceramic support member. The catalytic structure may be, for example, a sensor in which the catalytic coating catalyzes a gas phase reaction such as oxidation, the extent of which is monitored by temperature sensing means forming part of the sensor.

2. Related Art

Standard thick film technology involves screen printing a paste or ink that contains three components: an organic vehicle, a functional material (e.g., precious metal), and a glass frit or oxide. The organic vehicle provides a more or less homogeneous suspension of the functional material and imparts to the paste or ink a viscosity suitable for screen printing. The functional material is the ingredient that supplies the property needed for a particular application, e.g., platinum for an electrical or electronic circuit, or catalyst particles for promoting a chemical reaction such as oxidation. The glass frit supplies the bond between particles of the functional material (cohesion) and between the functional material and the substrate on which it is coated (adhesion). However, glass frits typically contain components such as boron, bismuth or lead which have negative effects on catalyst activity, selectivity and stability. Therefore, these materials are not of utility for many catalyst compositions.

U.S. Pat. No. 4,185,131, issued Jan. 22, 1980 to G. J. Goller et al and entitled "Screen Printing Method For Making an Electrochemical Cell Electrode", discloses fuel cell electrodes made on a continuous basis using screen printing. A wet floc of a co-suspension of carbon and hydrophobic polymer is dried and reduced to a fine powder and resuspended in an inking vehicle. The ink is then screen printed onto a porous substrate and the ink vehicle removed by heating. The resulting coating is compacted, sintered and then catalyzed, such as with platinum. Catalyzation of the sintered coating is stated to be carried out by the methods described in Katz et al U.S. Pat. Nos. 3,932,197 or 3,979,227.

U.S. Pat. No. 4,229,490, issued Oct. 21, 1980 to S. N. Frank et al and entitled "Novel Method For Catalyst Application to a Substrate For Fuel Cell Electrodes", discloses applying a platinum black plus graphite catalyst to a substrate by screen printing it onto a thin, carbonized paper-like substrate.

U.S. Pat. No. 5,273,779, issued Dec. 28, 1993 to I-Cherug Chen et al and entitled "Method of Fabricating a Gas Sensor and the Product Fabricated Thereby", discloses applying a buffer layer onto a substrate and applying at least one gas sensing layer atop the buffer layer. A pair of electrodes is disposed on the gas sensing layer and a catalytic layer is coated onto the gas sensing layer by a spin-casting process, using centrifugal force, to form thin and evenly deposited layers on the substrate.

The book *Principles of Chemical Sensors* by Jiri Janata, Plenum Press, New York, N.Y., 1989 (ISBN 0-306-43183-1), discloses at pages 51–53 thereof, catalytic gas sensors stated to be useful for the detection of sub-threshold concentrations of flammable gases in ambient air and finding use as a safety expedient in mining operations. A simple sensor is illustrated in FIG. 2–10 showing a support bead such as a pellet of thoria/alumina coated with a porous catalytic metal, palladium or platinum, and having a platinum coil embedded within the pellet. The coil is stated to act both as a heater and as a resistance thermometer but any type of temperature sensor is stated to be usable. When a combustible gas reacts at the catalytic surface, heat evolved from the reaction is stated to increase the temperature of the pellet and of the platinum coil, thus increasing its resistance. The latter is measured, for example, by use of a Wheatstone bridge.

An article entitled *Thick Film Pellistor Array With a Neural Network Post-Treatment* by H. Debéda et al was published by Elsevier Science S.A. in *Sensors and Actuators* B 26–27 (1995) at pages 297–300. This article discloses pellistor gas sensors and also notes that a typical pellistor consists of a platinum wire supported in an alumina bead impregnated with a finely dispersed noble metal such as palladium. As illustrated in FIG. 2 and discussed in paragraph 2, screen printed pellistors are made by screen printing a platinum resistor on one side of an alumina substrate and depositing a catalytic layer on the other side of the substrate, which catalytic layer is then fired. The method of depositing the catalytic layer is not specified.

SUMMARY OF THE INVENTION

The present invention broadly involves the use of compositions comprising one or more metal resinate compounds which can be used in a catalytic ink which, when fired to form a catalytic fired coating, will bind active catalyst particles to each other and to ceramic or other surfaces, such that the activity and selectivity of the catalyst are not compromised in the bound state. Thus, the metal resinate provides excellent adhesion and cohesion in the fired coating without significantly, or at all, adversely affecting catalytic performance.

In accordance with the present invention there is provided a catalytic structure comprising a support member on which is disposed a catalytic material comprising a fired coating of a catalytic ink. The catalytic ink is comprised of a liquid vehicle, at least one metal resinate compound comprising a metal moiety and an organic moiety, and has therein a catalytically effective amount of a catalytic metal component.

Another aspect of the invention provides for the metal moiety of the metal resinate to comprise at least a part of the catalytic metal component.

Another aspect of the invention provides for the catalytic ink to further comprise fine particles of a refractory metal oxide (support material).

Yet another aspect of the invention provides for at least a part of the catalytic metal component in the catalytic ink to be derived from a source other than the metal resinate and to be dispersed on the particles of refractory metal oxide.

In one aspect of the present invention there is provided a catalytic structure comprising a support member on which is disposed a catalytic material comprising a fired coating of a catalytic ink. The catalytic ink is comprised of a liquid vehicle, at least one metal resinate compound, and fine particles of a refractory metal oxide having dispersed thereon a catalytically effective amount of a catalytic metal component. For example, the metal of the catalytic metal component may be one or more platinum group metals and may be present in the amount (calculated as the elemental metal) of at least about 30 milligrams per square meter ( $mg/m^2$) of the fired coating, e.g., from about 30 to 9000 $mg/m^2$.

In one aspect of the invention, the support member comprises a ceramic material, the vehicle is an organic solvent and the metal resinate compound is selected from the group consisting of one or more of resinates of bismuth, calcium, chromium, cobalt, copper, iron, lead, lithium, manganese, nickel, palladium, platinum, potassium, rare earth metal, rhodium, silicon, silver, tin, zinc and zirconium. Reference to "rare earth metal" or "rare earth metals" means the fifteen elements of atomic numbers 57 through 71 inclusive, and includes lanthanum, cerium and praseodymium. Commercial products, such as the rare earth metal resinates, usually comprise a mixture of individual rare earth metal elements, with lanthanum and cerium usually predominating. As used herein and in the claims, "rare earth metal" resinate or resinates means and includes a resinate of a single rare earth metal, e.g., cerium, or resinates of two or more rare earth metals.

For example, the metal resinate compound may be selected from the group consisting of one or more of calcium resinates, zirconium resinates, and silicon resinates.

An aspect of the present invention provides for the catalyst structure to comprise a catalytic gas sensor wherein there is disposed on the support member in heat transfer relationship with the coating of catalytic ink at least one conductor member comprising temperature sensing means and electrical heating means.

Generally, the particle size may be any size suitable for screen-printing of the catalytic ink, i.e., the particles must be small enough to easily pass through the mesh of the printing screen. In one aspect of the present invention, the fine particles of refractory metal oxide have a mean diameter of not greater than about 20 microns and, preferably not greater than about 5 microns, and a size distribution such that at least 90 percent of the particles have a mean diameter of not greater than about 5 microns and at least about 95 percent of the particles have a mean diameter of not greater than about 10 microns.

In another aspect of the present invention, the refractory metal oxide is selected from the group consisting of one or more of alumina, ceria, ceria-zirconia, titania, silica, silicaalumina, silica-titania, zirconia, and thermally-stabilized versions thereof.

Yet another aspect of the present invention provides for a catalytic gas sensor comprising the following components. A support member is made of a thermally conductive and electrically insulative material and has a first major surface and a second, opposite major surface. A catalytic material is comprised of a fired coating of a catalytic ink, the catalytic ink being comprised of a liquid vehicle, and a catalytically effective amount of a catalytic metal component, e.g., at least one platinum group metal component, present in the fired coating in the amount of at least about 30 $mg/m^2$. The catalytic ink may optionally further comprise fine particles of a refractory metal oxide having dispersed thereon the catalytic metal component. Temperature-sensing means are disposed in heat-transfer relationship with the catalytic material and electrical heating means are disposed in heat-transfer relationship with the catalytic material.

One aspect of the invention provides for the fired coating to be disposed on the first major surface and both the temperature-sensing means and the electrical heating means to be embedded within the sensor, whereby heat transfer between the catalytic material and each of the temperature-sensing means and the electrical heating means is through at least a part of the thickness of the support member. With this particular arrangement, at least one of the temperature-sensing means is disposed directly opposite the catalytic material.

A method aspect of the present invention provides a method of making a catalytic structure, the method comprising the following steps. A catalytic ink is prepared by mixing a liquid vehicle and at least one metal resinate compound to provide a catalytic ink having thereon a catalytically effective amount of a catalytic metal component. The resulting catalytic ink is applied to a support member to provide an ink coating on a selected area of the support member, and is then fired to provide a fired coating of catalytic material on the selected area of the support member. The ink coating may be fired at a temperature of from about 500° C. to 1000° C., preferably 700° C. to 900° C.; for example, it may be fired by being heated to a peak temperature of about 700° C. to 900° C., e.g., 850° C.

An aspect of the method of the present invention may further comprise the steps of (1) impregnating a refractory metal oxide in fine particulate form with a liquid in which is dispersed the catalytic metal component or a precursor thereof; (2) drying and heating the thus-impregnated refractory metal oxide; and (3) mixing the dried and heated refractory metal oxide with the liquid vehicle and the metal resinate.

One method aspect of the present invention provides for the step of impregnating the refractory metal oxide to comprise preparing a solution of the catalytic metal component or a precursor thereof, e.g., one or more soluble compounds or complexes of one or more platinum group metals, and wetting the refractory metal oxide with the solution, and further provides for the step of heating the impregnated refractory metal oxide to comprise carrying out such heating in air at a temperature of from about 400° C. to 600° C.

In one method aspect the catalytic structure comprises a catalytic gas sensor and the method further comprises the step of affixing to the support member a conductor member comprising temperature sensing means and electrical heating means and disposing it in heat transfer relationship to the fired coating of catalytic material.

As used herein and in the claims, the following terms have the indicated meanings.

The term "ink" or "catalytic ink" shall mean and include inks and pastes; use of the word "ink" does not imply a limitation on viscosity that excludes pastes.

The term "a catalytically effective amount of a catalytic metal component in a catalytic ink" means an amount which, when the ink is applied in conventional thick film technology thicknesses, and fired to form a fired coating (of, e.g., from about 5 to 75, preferably 15 to 45 microns in thickness), will provide a discernible catalytic effect on the reaction of reactants contacted with the fired coating under reaction conditions.

The term "ceramic" is intended broadly to include suitable, high-temperature refractory support members including, without limitation, support members comprised of one or more metal oxides or one or more metal nitrides, for example, support members comprising alumina, either alone or in combination with various proportions of other metal oxides, silicon nitride, cermets and the like.

The term "rare earth metal" is defined above.

The term "platinum group metal" means and includes platinum, palladium, rhodium, iridium, osmium and ruthenium.

DETAILED DESCRIPTION OF THE INVENTION AND PREFERRED EMBODIMENTS THEREOF

Figure 1:
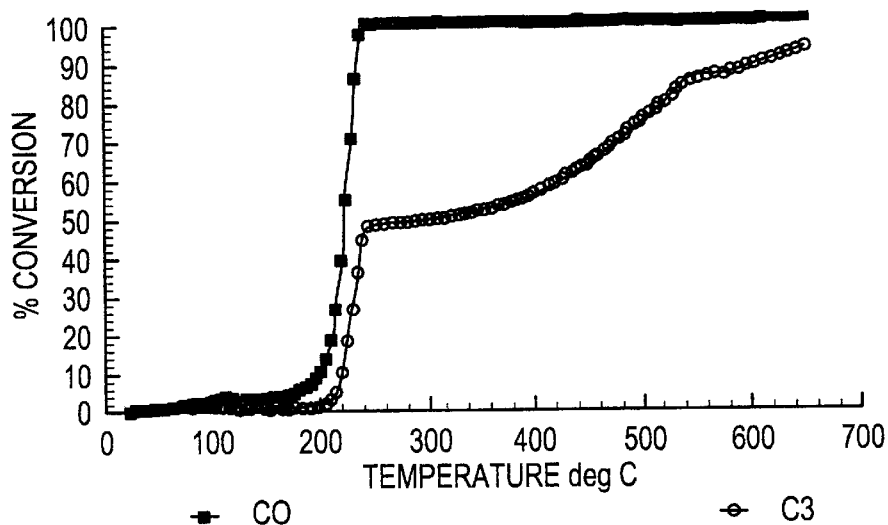
FIGS. 1 through 3 and 4 through 11 are graphs showing typical percent conversion-versus-temperature curves ("conversion curves") for oxidation of carbon monoxide and $C_3$ hydrocarbons in gas streams contacted under oxidizing conditions with various catalytic structures.

Metal resinates, sometimes referred to as "metal-organics" in the field of thick film technology, are, broadly speaking, compounds in which one or more positively charged metal ions are bound to one or more negatively-charged organic species, for example, metal salts of organic acids. A specific class of metal resinates are compounds comprising metal bonded to an organic residue through an oxygen atom, for example, metal salts of carboxylic acids or alcohols of the type found as a component, along with essential oils and terpenes, in natural resins. For example, metal resinates may comprise metal salts of acids such as 2-ethylhexanoic acid or trimethyl cyclohexanol, dissolved in an organic solvent. Metal resinates are usually made available commercially in a mineral spirits solvent or carrier. Metal resinates are, broadly speaking, oil-soluble compounds, and the resinates serve to carry the metal component or components in the form of a dissolved, rather than a particulate, component. With the metallic and semi-metallic elements, resinates are often coordination compounds or salts of organic acids. Resinates are also commonly made as compounds of metals with modified natural products such as sulfurated copaiba balsam. Such resinates, optionally mixed with solid metal oxide particles, such as particles of refractory metal oxides impregnated with one or more catalytic metal components ("particulate catalysts"), are applied as a catalytic ink coating on a substrate, such as the surface of a ceramic support member, e.g., a ceramic sensor. When such coated substrate is fired at high temperature, e.g., in air, the organic part of the resinates burns off to leave behind a fired coating comprising an interparticle inorganic network adhering to the substrate surface. Thus, the solid particles are bound together into a cohesive structure or coating as well as adhering to the substrate surface. The thickness of the fired coating obtained from the catalytic ink may vary, but is usually from about 5 to 75, preferably 15 to 45, microns in thickness. The catalytic metal loading may vary widely, for example, from about 30 to 9000 milligrams per square meter of fired coating ("$mg/m^2$").

The catalytic metal may be introduced into the catalytic ink either as the metal moiety of the metal resinates, or by being impregnated into the fine particles (powder) of refractory metal oxide support material, i.e., as part of a particulate catalyst. The catalytic metal or metals may, of course, be introduced both as the metal moiety of the metal resinates and impregnated into the refractory oxide support material. In one embodiment, the support material powder may be omitted and the catalytic metal introduced as the metal moiety of the metal resinates of the catalytic ink. However, the presence of a fine, particulate refractory metal oxide support material is preferred. These support material particles, which are selected to have a relatively high surface area, enhance the catalytic effectiveness of the fired coating by providing a high surface area support for the catalytic metals. For example, gamma alumina particles usually have a surface area of from about 100 to 200 square meters per gram.

Thus, the present invention could be carried out by introducing one or more catalytic metals as the metal moiety of the metal resinates and adding a non-metallized refractory metal oxide support powder to the catalytic ink. In preparing the catalytic ink, the metal resinates will be dispersed on and impregnated into the support material particles so that the fired coating obtained by calcining the catalytic ink coated onto a substrate will have the metal moiety of the metal resinates well-dispersed on the refractory metal oxide support material particles. With this technique, sufficient solvent is used in the catalytic ink to insure that the viscosity of the metal resinate is low enough to thoroughly impregnate the particles of refractory metal oxide support material. Alternatively, or in addition, the support material particles may, prior to being introduced into the catalytic ink, be impregnated with soluble compounds or complexes of the catalytic metals and calcined to provide the catalytic metal component dispersed on and impregnated into the support material particles.

A combination of the foregoing techniques may also be employed.

For a given particulate catalyst, appropriate metal resinate compounds provide good cohesion of the particles to each other, good adhesion of the particles to a substrate, and good catalytic activity. A particular metal resinate or mixture of metal resinates which provides the desired properties for a given particulate catalyst can be determined by routine testing. Thus, a composition comprising one or more metal resinate compounds can be used to adhere particulate catalyst particles to ceramic, metal, or other suitable support members without negatively affecting the performance of the catalyst. In contrast, although typical glass frit compositions give good adhesion and fair cohesion characteristics to fired catalytic ink coatings, they often have highly negative effects on catalyst performance.

In the present invention, the metal resinate compositions are blended together with the catalyst particles and a suitable organic vehicle to create a screen printable paste or ink (collectively referred to below as an "ink" or "catalytic ink"). This ink is then screen printed or otherwise applied to a suitable substrate, i.e., a support member such as the surface of a sensor. The resulting item is dried to remove highly volatile organics and fired, i.e., heated in a furnace, e.g., in a belt furnace, with an appropriate temperature profile to burn off the organics and form the fired catalytic coating.

EXAMPLE A

Preparation of Materials

I. Catalytic Ink Preparation

Catalytic ink preparation was done by standard thick film procedures. Typically, to make ink, 6 grams of finely divided particulate catalyst was combined with 1 to 4 grams of glass frit and/or one or more metal resinate compounds. To this mixture was added sufficient organic medium vehicle to wet the solid particles and to adjust the viscosity of the ink to appropriate values. The mixture of catalyst, frit or metal resinate and medium would typically be approximately 10 to 12 grams in total. This mixture was then passed repeatedly through a three roll mill until the mixture was of uniform consistency.

Preparation of the particulate catalyst was prepared by the well-known conventional measures of impregnating a suitable fine refractory metal oxide powder with a solution of one or more soluble catalytic metal compounds or complexes. The impregnated particles were then dried and calcined in air. The refractory metal oxide support such as many suitable supports such as mentioned above, including alumina, ceria-zirconia, ceria, zirconia, etc. The catalytic metal components may comprise any suitable catalytic metals, whether in elemental, alloy or compound, e.g., oxide, form, as is well-known in the art. Platinum group metals, especially platinum, palladium or rhodium, or combinations of two or more thereof, may be employed. Base metal catalytic components, e.g., nickel, iron, cobalt, cerium and manganese, are among many metals known for catalytic efficacy for particular purposes.

As is well-known in the art, the supports may be stabilized against thermal degradation by impregnation of the supports with a stabilizing material. For example, alumina support particles may be stabilized against thermal degradation by impregnation thereof with a soluble cerium salt followed by calcination to convert the impregnated cerium salt to ceria. Similarly, it is known to stabilize zirconia particles by impregnation with a soluble cerium salt solution, followed by calcination, to provide ceria dispersed in the zirconia matrix to thermally stabilize the same. Conversely, it is also well-known in the art to thermally stabilize ceria particles by impregnating them with a solution of a soluble aluminum compound, followed by calcination to convert the impregnated aluminum compound to alumina. For example, see U.S. Pat. No. 4,714,694 issued on Dec. 22, 1987 to C. Z. Wan et al, and entitled "Aluminum-Stabilized Ceria Catalyst Compositions, and Methods of Making the Same". The disclosure of this Patent is hereby incorporated by reference herein. The treatment of refractory metal supports to stabilize them against thermal degradation is discussed at column 2, lines 7–26, of U.S. Pat. No. 4,714,694, wherein it is described as a known expedient in the art to stabilize an alumina support against thermal degradation by the use of materials such as zirconia, titania, alkaline earth metal oxides such as baria, calcia or strontia or, most usually, rare earth metal oxides, for example, ceria, lanthana and mixtures of two or more thereof. Reference in this regard is made to U.S. Pat. No. 4,171,288 of Carl D. Keith et al. The stabilizing oxides are impregnated into the alumina supports from solutions of soluble compounds or complexes of metals followed by calcination to convert the impregnated compound to the oxide. Calcination is usually carried out in air at temperatures of about 350° C. to 600° C. In U.S. Pat. No. 4,714,694, particles of ceria or a ceria precursor are impregnated with a liquid dispersion, i.e., a solution or suspension, of an aluminum stabilizer precursor, e.g., a soluble aluminum compound, followed by calcination of the impregnated ceria particles.

II. Adhesion and Cohesion Testing

Adhesion and cohesion of the fired catalytic coatings on ceramic coupons were tested by screen printing a circle or square of the catalytic ink on coupons of 96% alumina (supplied by Coors Ceramic Co., Electron Products Group, Grand Junction, Colo.), or 100% alumina, or silicon nitride. The screen printed piece was dried in an oven for fifteen minutes at 125° C. and then fired at 850° C. for 10 minutes by using a belt furnace to provide a fired coating of catalytic ink. Adhesion and cohesion were determined by pressing a piece of cellophane tape on top of the fired coating and quickly removing the tape. Alternatively, the fired coating was mechanically scraped with a metal tool such as a spatula. Microscopic examination helped determine how strongly the fired coating of catalytic ink adhered to the substrate and how easily layers of the fired coating were removed.

III. Preparations of Metal Resinates and Catalytic Material Combinations

In a crucible the desired metal resinates were mixed with enough toluene to reduce the viscosity to a low level and insure even distribution of the metal resinates through the surface of the catalytic material to be added. The desired quantity of catalytic material powder, which had been prepared by calcining at 850° C. refractory metal oxide particles which had been impregnated with a solution of soluble catalytic metal salts or complexes, was added to the resinates. The contents of the crucible were mixed well. The crucible was then placed in an oven at 100° C. for at least 2 to 3 hours, then was transferred to a furnace and the temperature was slowly raised to 250° C., where it was held for 10 minutes. Then the temperature of the furnace was slowly raised to 850° C. and held at this temperature for an additional 10 minutes. The crucible was then removed from the oven and cooled in air. Four grams of the resulting solid was slurried with sufficient water to reduce the solids level of the slurry to 45% by weight. This slurry was then used to coat a monolith honeycomb carrier. The coated monolith carrier was then calcined at 850° C. for 10 minutes.

IV. Preparations With Frit

The following is the general preparation procedure used to prepare a melting frit. Four grams of catalyst and 0.8 grams of frit were slurried with water to 45% by weight solids. Two types of low melting frit were used. Frit A comprised, by weight, about 75 to 85% $Bi_2O_3$, about 2 to 3% $Al_2O_3$, about 8 to 12% $B_2O_3$ and about 5 to 10% $SiO_2$. Frit B comprised a lead borosilicate glass powder containing 73% by weight lead and obtained from Cerdec/Drakenfeld Corporation of Washington, Pa.

V. Applying the Catalytic Material as a Coating on a Honeycomb-Like Monolith Carrier For Test Purposes Testing of catalytic performance of catalytic powders and catalytic powders plus frits was sometimes done by applying the material to a monolith honeycomb carrier. In the case of catalytic material powders and catalytic material powders plus frits, four grams (dry basis) of the catalytic material powder, or four grams of a mixture of catalytic material powder plus frit, were combined with enough water to make a 45% by weight solids slurry. The resulting slurry was homogenized with a magnetic stirrer and then transferred to a one-ounce (liquid) capacity plastic vial fitted with a snap cap. A weighed ceramic (cordierite) honeycomb-type monolith carrier in the shape of a cylinder with dimensions 1 inch (2.54 cm) high×¾ inch (1.91 cm) in diameter and a cell density of 400 cells per square inch (62 cells per square centimeter) was placed into the plastic vial. (The "cell density" refers to the number of parallel gas-flow channels per square inch of end face of the carrier.) The vial was inverted several times to ensure that the slurry passes through all the channels of the monolith to coat the walls thereof. The monolith was then removed from the vial and excess slurry was removed with an air knife. The monolith was weighed to determine if the appropriate amount of coating had been applied. After the coating weight was found to be acceptable, the monolith was dried at 120° C. Then the monolith was placed in a crucible and the crucible was placed into a furnace. The temperature of the furnace was raised to 850° C. and held at that temperature for 10 minutes. The crucible was then removed from the furnace and allowed to cool to room temperature. All coated-monolith samples received the foregoing treatment. The cooled monolith was weighed and the weight of dry coating of catalytic material was determined by subtracting the weight of the uncoated monolith from the weight of the coated monolith. The weight (dry basis) of the coating of the catalytic material on the monoliths was about 0.6 gram (which is equivalent to 2.0 grams per cubic inch of volume of the coated monoliths).

EXAMPLE B

Performance Testing to Compare Catalysts with the Calcined Residue of Catalytic Inks The catalyst performances of monoliths coated with the calcined residue of catalytic inks reported in the following examples were evaluated. In each case, a catalytic ink was prepared by combining a catalytic powder with selected resinates and, if necessary, solvent. That material was then calcined to remove the organic constituents and thereby decompose the catalytic ink. The calcined material was then coated onto the gas flow passages of suitable ceramic monolith, as described below. In other cases, the same catalytic powders were coated onto the gas flow passages of such monoliths. The samples were all evaluated using a laboratory test reactor and the following procedure. A gas stream containing the reactants of interest (an oxidant, carbon monoxide and hydrocarbons comprising a mixture of propane and, as the unsaturated hydrocarbon, propene) at the desired concentrations was generated. The gas stream was then heated to the desired temperature, and passed over the catalyst (either coated on a monolith or as a powder) contained in a quartz tube at the desired temperature. The concentrations of hydrocarbon and carbon monoxide both upstream and downstream of the catalyst were monitored using hydrocarbon, carbon monoxide and carbon dioxide sensors obtained from Rosemount Analytical, Inc., La Habra, Calif.

Approximately 0.6 gram of catalytic material was coated, as described above, onto a cordierite monolith in the form of a cylinder approximately 1 inch long and 3/4 inch in diameter. The cylindrical side of the monolith was wrapped with a belt of ceramic "felt" to prevent gas by-pass around the side of the monolith, i.e., to insure that all the gas flows through the gas-flow channels of the monolith to contact the catalytic material coated on the walls thereof. The wrapped monolith was then inserted into a quartz reactor tube. The quartz reactor tube is placed in a programmable tube furnace whose temperature is controlled by a thermocouple in a quartz thermowell suspended just above the catalyst being tested.

Gases were fed to the reactor tube using mass flow controllers. A static mixer was used to insure good mixing of the feed gases and a syringe pump was used to feed water to a vaporizer to allow inclusion of steam in the feed stream, if desired. The combined feed gases were passed over the catalyst at 5–6 psig.

At the exit to the reactor, any water vapor was removed from the exit gas stream by passing the exit gas stream through a mini gas sampling system (MG-1220-S1-10) apparatus sold under the trademark PERMA PURE by Perma Pure Inc. of Toms River, N.J. This apparatus comprises a water-permeable membrane through which only the water content of the tested gas stream passes for removal by a nitrogen carrier gas. The dried exit gas stream was then directed to three different Rosemount analyzers: one to analyze for total hydrocarbon content, one for carbon monoxide content and one to analyze for carbon dioxide content.

In a typical experiment, a "conversion curve" (often referred to as a "light-off" curve) of feed species versus temperature was generated. The conversion was obtained by raising the temperature of the reactor in a controlled linear fashion from ambient or near ambient to 600 to 700° C. and noting the change, if any, of reactant concentration in the product gas as a function of temperature. Typically, one analytical result was recorded every 20 seconds. The conversions (oxidation) of unsaturated hydrocarbon and carbon monoxide were calculated by measuring the differences in, respectively, the hydrocarbon and carbon monoxide contents of the feed (to the catalyst) and exit (from the catalyst) test gas streams. These conversions were plotted versus temperature of the inlet gas stream to the catalyst to generate a conversion curve. Percent conversion for any reactant species is defined as the difference between the concentration of the species in the feed gas to the catalyst and the concentration of the species in the exit gas from the catalyst, divided by the concentration of the species in the feed gas, all multiplied by 100.

Typical Reactor Conditions
1. Flow Rates
Total Dry Flow (excluding water vapor) is 3000 cubic centimeters per minute ("cc/min") at a standard temperature and pressure ("STP") of 25° C. and 1 atmosphere, and includes an air flow of 40 to 75 cc per minute at STP. Space Velocity: 25,000 per hour at STP. Total wet flow (including water vapor): 3408 cc/min at STP.
2. Temperature
Temperature Ramp Rate: 15° C./minute
3. Composition of Test Gas
Carbon Monoxide Concentration: 1400 to 1700 ppm by volume Total Hydrocarbon Concentration: 900 to 1000 ppm by volume, on $C_1$ basis.
Hydrocarbon Composition: Propane and Propene in a molar ratio of 52:48 Propane:Propene. Nitrogen: balance
Test Results—Coated Monoliths
The following examples describe the performance test results obtained as described above in Example B. Resulting conversion curves for the tested coatings of the catalysts and the calcined residues of catalytic inks are shown in FIGS. 1 through 11.

EXAMPLE 1

A. Catalyst A was prepared according to the following procedure. 46.6 grams of an aqueous solution of platinum amine hydroxide salt (18.54% by weight Pt) was diluted with 15 ml of water. This solution was impregnated into 123.6 grams of gamma-alumina powder. 3.7 ml of acetic acid was mixed into the impregnated solid. 1.5 grams of an aqueous solution of platinum amine hydroxide salt (18.54% Pt) was diluted with 23.6 ml water and added to 92.8 grams of ceria-zirconia powder. The ceria-zirconia powder comprised ceria particles impregnated with zirconia, the zirconia comprising about 20% by weight ceria and 80% by weight zirconia. 2.8 ml of acetic acid was mixed into the impregnated solid.

B. The two impregnated solids were placed in a jar with grinding media and 187 ml of water. The jar was rolled on a mill for 20 minutes.

C. 18.5 grams of an aqueous rhodium nitrate solution (10.08% Rh) was diluted with 43.3 grams water. The resulting solution was added to 123.6 grams of gamma-alumina. 4.5 grams ethanolamine was mixed into the impregnated solid. The solid was added to the solids that were previously milled. The resulting slurry was milled for 2 hours. Then 35 grams of zirconium hydroxide (27% solids) and 2 drops of defoamer were added to the milling jar. The mixture was milled until the average particle size was approximately 5 microns. The resulting slurry was placed into a rotary evaporator and the water was removed. The resulting solid was dried in an oven at 100° C.

D. Catalyst A was coated onto a ceramic monolith and tested according to the procedure described above. The resulting conversion curve is shown in FIG. 1. It is seen that at a temperature from about 180° to 220° C., the conversion of carbon monoxide rapidly increases and attains 100% conversion at about 220° C. The conversion of the $C_3$ hydrocarbons begins to increase dramatically at about 220° C. and about 90% conversion is attained at a temperature of about 650° C.

EXAMPLE 2

A. Catalyst A of Example 1 was combined with 20% by weight of Frit A of Part IV of Example A, and a screen printable catalytic ink was prepared according to the procedure described above in Part I of Example A, using ethyl cellulose as the vehicle to provide a catalytic ink comprising 70% by weight Catalyst A, 14% by weight Frit A, and 16% by weight vehicle. Screen printing a pattern of this catalytic ink onto coupons of 96% alumina or coupons of silicon nitride, gave very good adhesion of the catalyst to the substrate surface as determined by the adhesion tests described in Part II of Example A.

Figure 2:
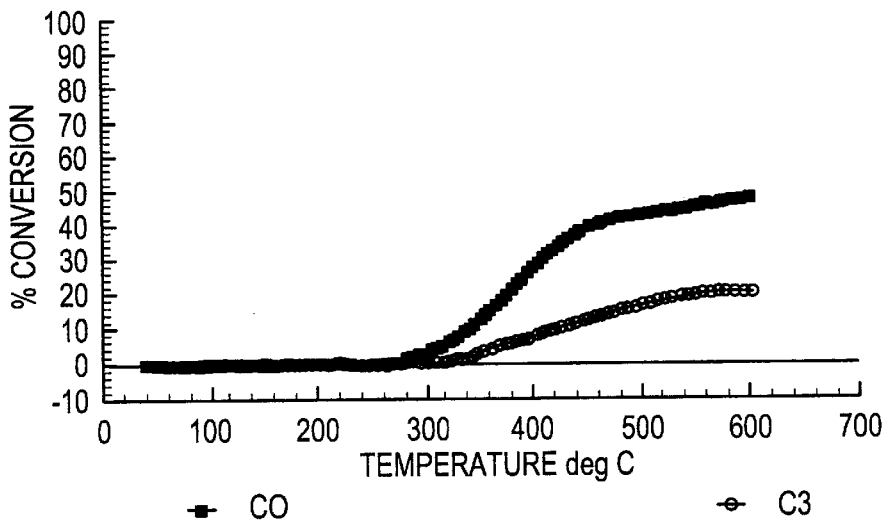

B. Catalyst A of Example 1 was combined with Frit A according to the procedure of Part III of Example A, and the catalyst plus frit combination was coated onto a ceramic monolith, using the procedure described above in Part V of Example A. The results of catalytic performance testing of this sample are shown in FIG. 2. Clearly the Frit A had a large negative impact on the catalyst activity for carbon monoxide and hydrocarbon conversion. Thus, significant oxidation of carbon monoxide and the hydrocarbon does not begin until a temperature of 300° C. has been exceeded and at a temperature of about 610° C. only about 20% conversion of the hydrocarbons and 55% conversion of the carbon monoxide has been attained.

EXAMPLE 3

A. A quantity of 12 grams of Catalyst A of Example 1 was combined with 2 grams of calcium resinate RI223, 2.0 grams zirconium resinate RI219 and 1.0 gram silicon resinate OL28FC. A screen printable catalytic ink was prepared according to the procedure described above. Screen printing a pattern of the catalytic ink onto 96% alumina or silicon nitride gave very good adhesion of the catalyst to the substrate surface, as determined by the adhesion tests of Part II of Example A.

Figure 3:
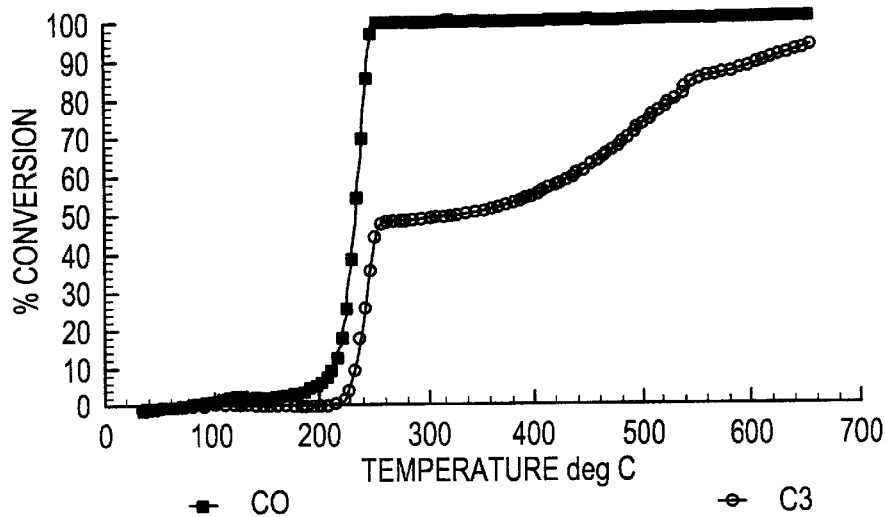
Figure 3A:
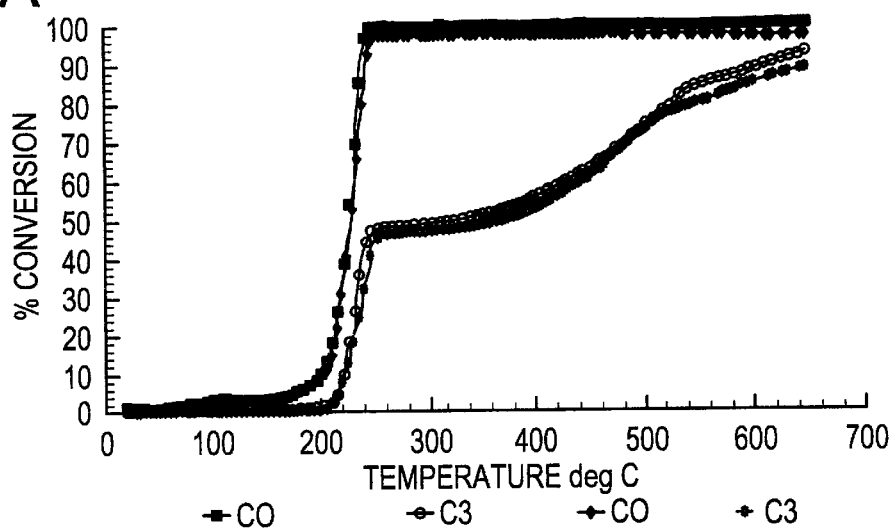
FIG. 3A is a graph on which the conversion curves of FIGS. 1 and 3 are superposed.

B. A quantity of 12 grams of Catalyst A of Example 1 was combined with 2 grams of calcium resinate RI223, 2.0 grams zirconium resinate RI219 and 1.0 grams silicon resinate OL28FC according to the procedure of Example A, Part III. The catalyst plus metal resinate combination was coated onto a ceramic monolith using the procedure of Example A, Part V. The results of catalytic performance testing of this sample are shown in FIG. 3. The inclusion of the metal resinate binder in the composition had little or no effect on catalyst performance. This can be seen clearly from FIG. 3A, which is a superposition of FIG. 1 onto FIG. 3, and it is seen that the conversion curves of the two tests substantially overlie each other.

EXAMPLE 4

Catalyst B was prepared according to the following procedure. Gamma-alumina powder was calcined at 850° C. for 30 minutes. 22.9 grams of a platinum amine hydroxide salt solution (18.85% Pt) was diluted with 7 grams of water. The Pt salt solution was impregnated into 61.8 grams of calcined alumina. Then 1.9 ml of acetic acid was mixed into the impregnated solid. 0.74 grams of the above platinum amine hydroxide salt solution was diluted with 13 grams of water and then impregnated onto 46.4 grams of ceria stabilized zirconia. 1.4 ml of acetic acid was then mixed into the impregnated ceria zirconia. The impregnated alumina and the impregnated ceria zirconia were placed into a jar with grinding media. Enough water was added to make a slurry of 40 to 50% solids. This slurry was milled for 20 minutes.

9.0 grams of aqueous rhodium nitrate solution (10.37% Rh) was diluted with 22 grams water. This was impregnated onto 61.8 grams calcined alumina. Following impregnation, 2.3 grams of monoethanolamine were mixed into the solid. The rhodium impregnated alumina was added to the milled slurry. Additional water was added to make the slurry 40 to 50% solids. Five grams of dry zirconium hydroxide was added. Milling was continued until the median particle size was 5 microns or less.

Figure 4:
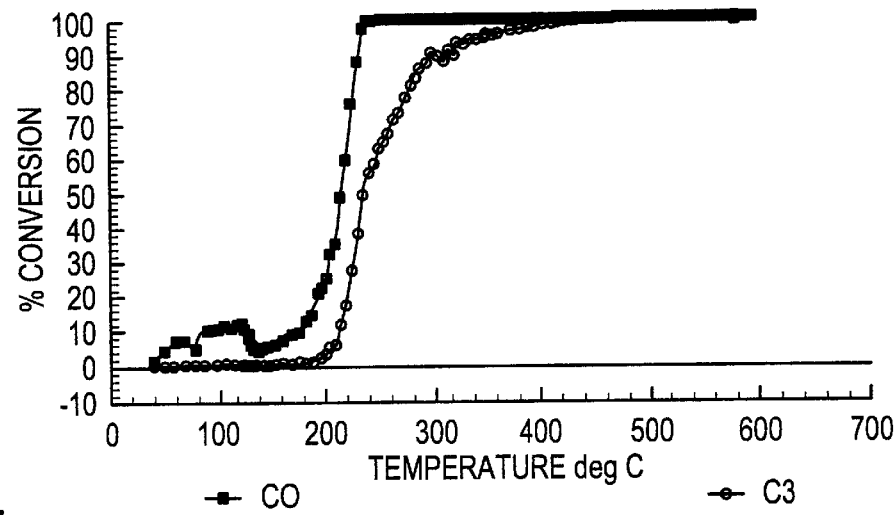

Catalyst B was coated onto a ceramic monolith according to the procedure of Part V of Example A. Catalyst B performance was determined using the catalyst test apparatus with the standard procedure described above. The resulting conversion curve is shown in FIG. 4 wherein it is seen that 100% conversion of carbon monoxide is attained at about 220° C. and that conversion of the hydrocarbon rapidly increases at about that temperature and attains 100% conversion at about 400° C.

EXAMPLE 5

A. A quantity of 6 grams of Catalyst B of Example 4 was combined with 1.5 grams of zirconium resinate RI219, and 1.0 gram of rare earth resinate, as supplied by Mooney Chemicals, Inc. of Cleveland, Ohio, under the description "Metal Carboxylates of Rare Earths." A screen printable catalytic ink was prepared according to the procedure described above in Part I of Example A. Screen printing a pattern of this catalytic ink onto 96% alumina or silicon nitride gave very good adhesion of the catalyst to the substrate surface as determined by the adhesion tests of Part II of Example A.

Figure 5:
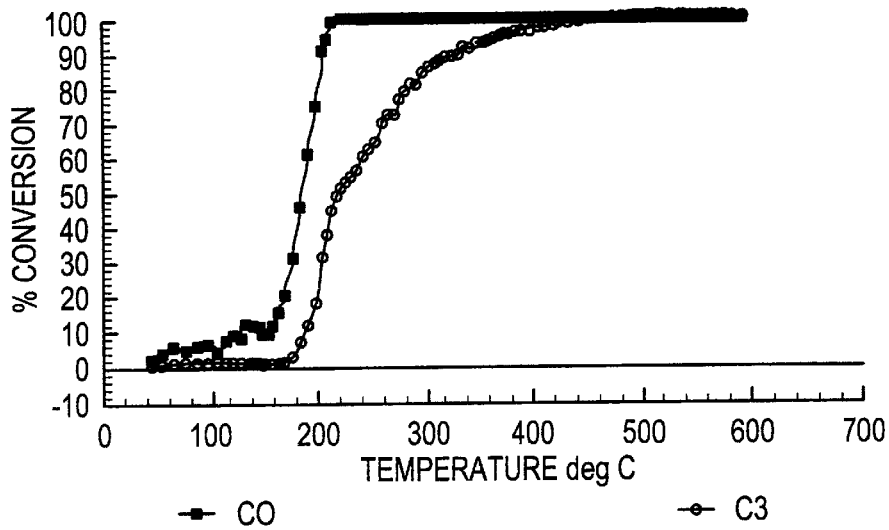

B. Catalyst B was combined with 1.5 grams of zirconium resinate RI219, and 1.0 grams of rare earth resinate according to the procedure described in Part III of Example A. The catalyst plus metal resinate combination was coated onto a ceramic monolith using the procedure of Part V of Example A. The results of catalytic performance testing of this Example are shown in FIG. 5. The performance of the catalyst plus metal resinate binder had little or no effect on catalyst performance. The conversion curve of FIG. 5 is quite similar to that of FIG. 4, with 100% conversion of the carbon monoxide being attained at about 200° C. and the oxidation of the hydrocarbon increasing rapidly at about that temperature to attain 100% conversion at a temperature of about 450° C.

EXAMPLE 6

Catalyst C was prepared according to the following procedure. 57.5 grams of an aqueous solution of platinum amine hydroxide salt (15.5% Pt) was impregnated into 216.4 grams of ceria stabilized zirconia. 6.5 ml of acetic acid was mixed into the impregnated solid. The impregnated solid was placed in a jar mill with 230 ml water and milled for several minutes.

18.5 grams of aqueous rhodium nitrate solution (10.08% Rh) was diluted with 12.4 grams water. The resulting solution was impregnated onto 123.6 grams of ceria stabilized zirconia. 4.4 grams of monoethanolamine was mixed into the impregnated solid. This material was added to the mill and the slurry was milled for several minutes. 36.6 grams of zirconium hydroxide paste (27% solids), 2 drops of defoamer and 3 ml of concentrated nitric acid were added to the mill and the mixture was milled for 15 minutes. The slurry was transferred to a rotary evaporator where the water was removed. The resulting solids were oven dried at 100° C.

Figure 6:
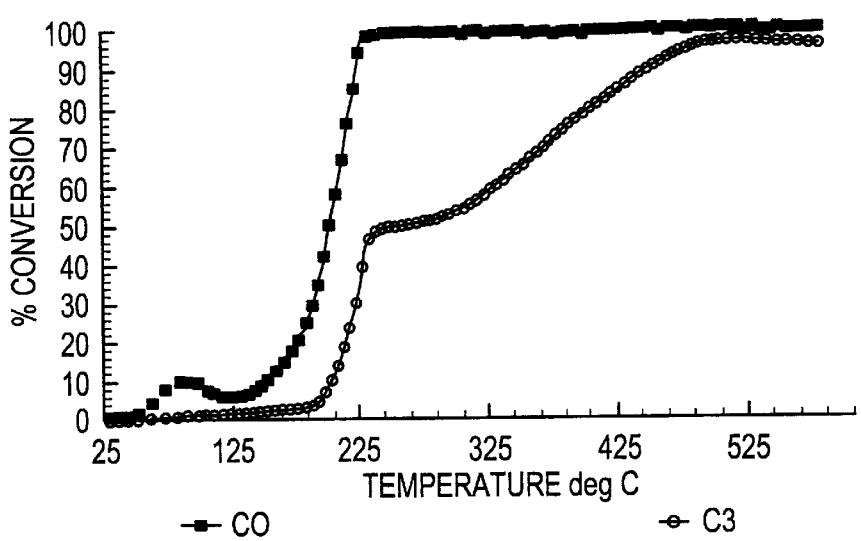

Catalyst C was coated onto a ceramic monolith according to the procedure described above in Part V of Example A. Catalyst C performance was determined using the catalyst test apparatus with the standard procedure described above in Example B. The resulting conversion curve is shown in FIG. 6. FIG. 6 shows a rapid increase in conversion (oxidation) of carbon monoxide starting at about 135° C. and attaining 100% conversion at a temperature of about 205° C. The hydrocarbon begins to show a rapid increase in conversion starting at a temperature of about 190° C. and attains about 95% conversion at a temperature of about 485° C.

EXAMPLE 7

A. Catalyst C was combined with 20% by weight of Frit A and a screen printable catalytic ink was prepared from the combination according to the procedure described in Part I of Example A. Screen printing a pattern of this catalytic ink onto 96% alumina or silicon nitride coupons gave very good adhesion of the catalyst to the substrate surface, as determined by the adhesion tests of Part II of Example A.

Figure 7:
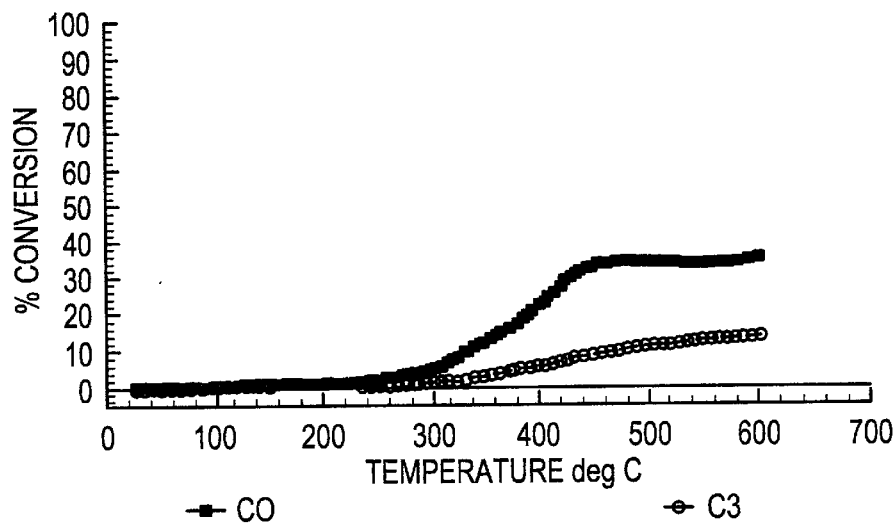

B. Catalyst C was combined with Frit A according to the procedure described in Part III of Example A and the catalyst plus frit combination was coated onto a ceramic monolith using the procedure of Part V of Example A. The results of catalytic performance testing of this sample are shown in FIG. 7 wherein no significant oxidation is noted until about 300° C., at which point the carbon monoxide oxidation begins to gradually increase and attains a maximum of a bit over 30% at a temperature range between about 440° to 600° C. Hydrocarbon conversion is worse and attains a maximum of about 10% at 600° C. Clearly the frit had a large negative impact on the catalyst activity for carbon monoxide and hydrocarbon conversion.

EXAMPLE 8

Catalyst D, consisting of rhodium supported on ceria-stabilized zirconia particles was prepared according to the following method. 10.8 grams of aqueous rhodium nitrate solution (10.08% Rh) was impregnated into 40 grams of ceria-stabilized zirconia. The resulting solid was combined with enough water to make a slurry of 40–50% solids. This slurry was ball milled for 45 minutes. Following the ball milling, a rotary evaporator was used to remove water from the slurry. The resulting solid was dried in an oven at 120° C.

Figure 8:
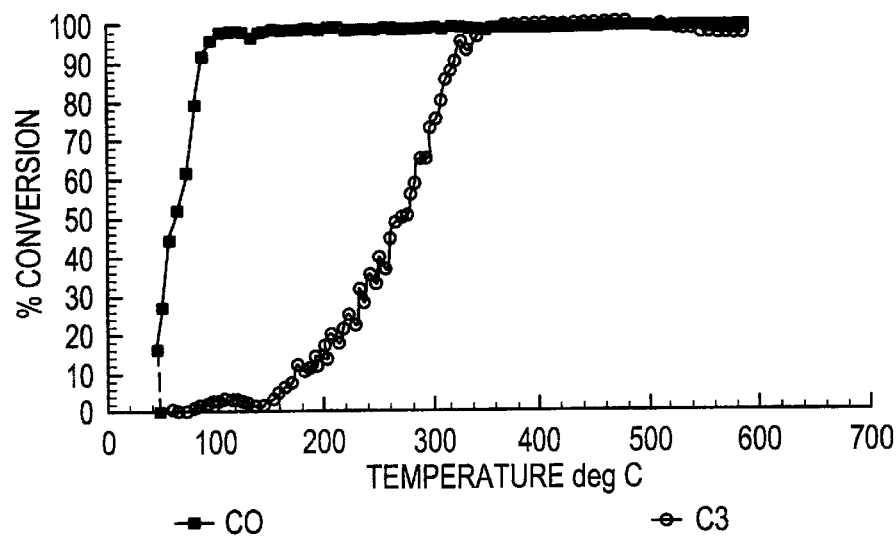

Catalyst D was coated onto a ceramic monolith according to the procedure of Part V of Example A. The performance of Catalyst D on this sample was determined using the catalyst test apparatus with the standard procedure described above in Example B. The resulting conversion curve is shown in FIG. 8, wherein carbon monoxide oxidation increases extremely rapidly starting at about 50° C. and attains about 98% or 99% conversion at about 100° C. That high level of conversion is maintained at higher temperatures. The hydrocarbon conversion begins to increase at about 150° C. and attains about 97% to 98% conversion at about 330° C. and maintains substantially that high level of conversion at higher temperatures.

EXAMPLE 9

A. Catalyst D was combined with 20% by weight of Frit A and a screen printable catalytic ink was prepared according to the procedure described above. Screen printing a pattern of this ink onto 96% alumina or silicon nitride coupons gave very good adhesion of the catalyst to the substrate surface based on the performance of adhesion tests according to Part II of Example A.

Figure 9:
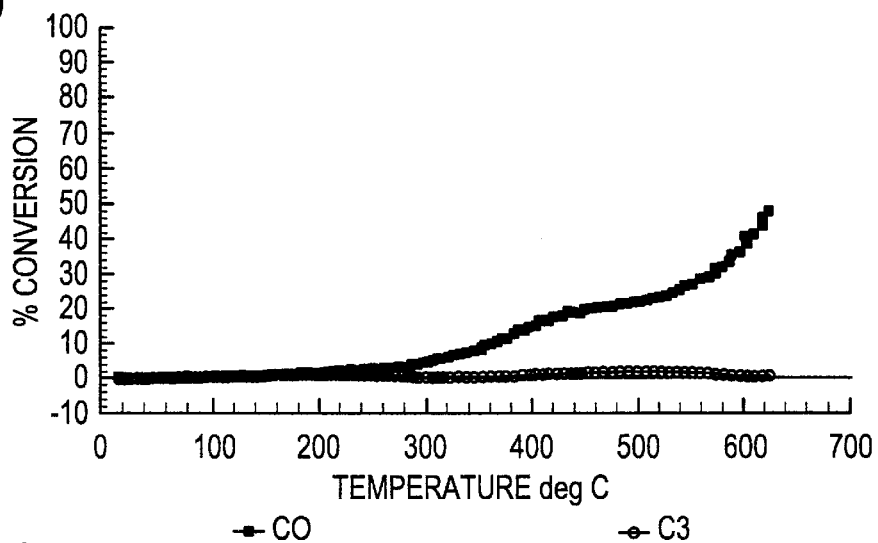

B. Catalyst D was combined with Frit A according to the procedure of Example A, Part III. The catalyst plus frit combination was coated onto a ceramic monolith using the procedure of Part V of Example A. The results of catalytic performance testing are shown in FIG. 9 wherein no significant oxidation is noted until about 290° C., when the carbon monoxide oxidation gradually increases to a maximum of about 55% at a temperature of about 620° C. Substantially no hydrocarbon conversion is attained. Clearly the frit had a large negative impact on the catalyst activity for carbon monoxide and hydrocarbon conversion.

EXAMPLE 10

A. Catalyst D was combined with 20% by weight of Frit B and a screen printable catalytic ink was prepared according to the procedure described above in Part I of Example A. Screen printing a pattern of this catalytic ink onto 96% alumina or silicon nitride coupons gave very good adhesion of the catalyst to the substrate surface, as determined by the adhesion tests of Part II of Example A.

Figure 10:
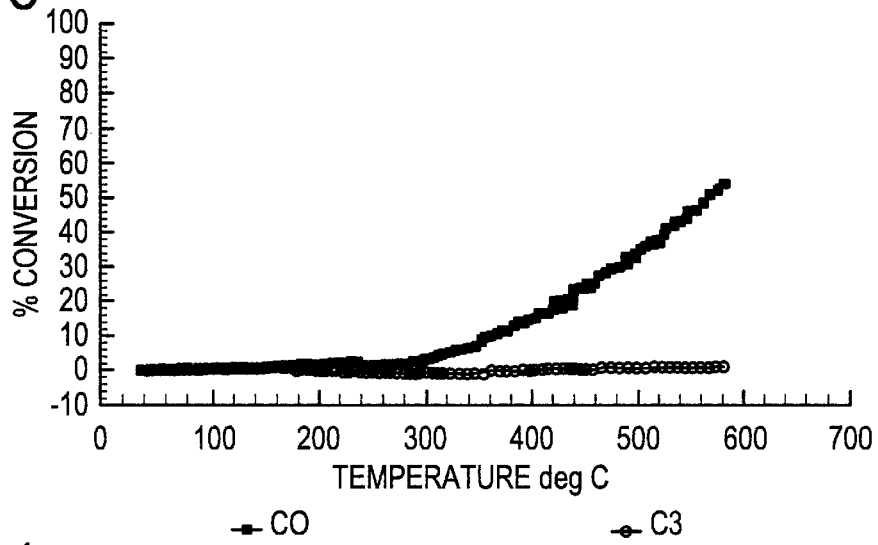

B. Catalyst D was combined with Frit B according to the procedure of Example A, Part III. The catalyst plus frit combination was coated onto a ceramic monolith using the procedure of Part V of Example A. The results of catalytic performance testing of this sample are shown in FIG. 10, which is substantially similar to FIG. 9, as FIG. 10 shows significant oxidation of carbon monoxide commencing at about 300° C. but attaining a maximum of about 55% at 600° C., and substantially no oxidation of the hydrocarbon.

Clearly the frit had a large negative impact on the catalyst activity for carbon monoxide and hydrocarbon conversion.

EXAMPLE 11

A. Catalyst D, 6 grams, was combined with 1.0 gram Ca resinate RI223, 1.0 gram zirconium resinate RI219 and 0.5 grams silicon resinate 0228FC. A screen printable catalytic ink was prepared according to the procedure described in Example A, Part I. Screen printing a pattern of this ink onto 96% alumina or silicon nitride coupons gave very good adhesion of the catalyst to the substrate surface as determined by the adhesion tests of Part II of Example A.

Figure 11:
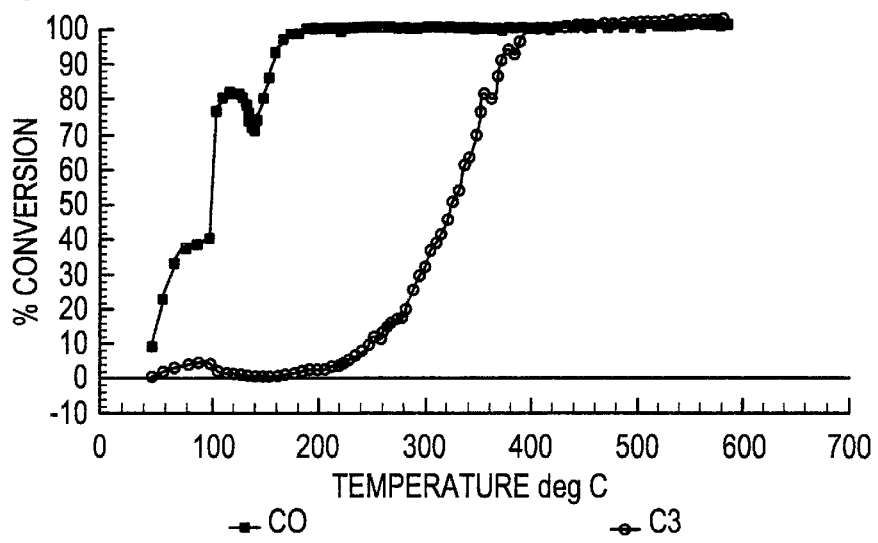

B. Catalyst D, 6 grams, was combined with 1.0 gram Ca resinate RI223, 1.0 gram zirconium resinate RI219 and 0.5 gram silicon resinate 0228FC according to the procedure of Example A, Part III. The catalyst plus metal resinate combination was coated onto a ceramic monolith using the procedure of Part V, Example A. The results of catalytic performance testing of this sample are shown in FIG. 11, wherein oxidation of carbon monoxide begins to be noticeable at a temperature as low as about 40° C. and rapidly increases to attain substantially 100% conversion at a temperature of about 190° C. Hydrocarbon conversion begins at about 70° C., drops off to substantially zero in the temperature range of about 110° to 200° C., and then increases fairly rapidly until 100% conversion is attained at a temperature of about 395° C. The inclusion of the metal resinate in the composition had little or no effect on catalyst performance.

Figure 12:
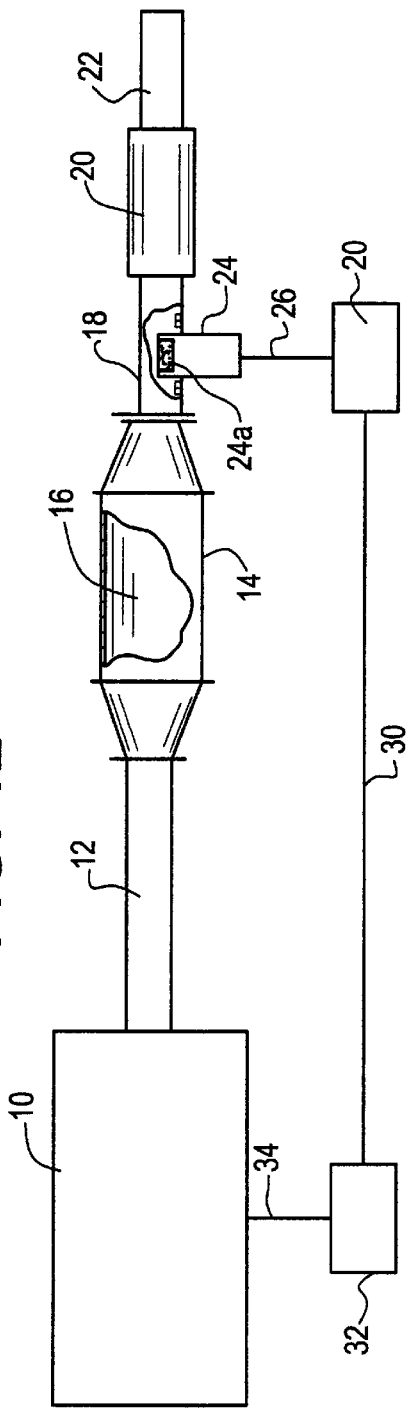
FIG. 12 is a schematic diagram showing one environment of use of an embodiment of a catalytic structure of the present invention comprising a catalytic gas sensor disposed in the exhaust line of an engine fueled by a hydrocarbon-aceous fuel such as gasoline, diesel oil or natural gas.

Referring now to FIG. 12, there is shown a schematic illustration of one environment of use of a gas sensor embodiment of the catalytic structure of the present invention. Sensor 24 may be made of thin layers of alumina separated by metallized layers providing the heaters and resistance thermometers, with both outer layers of the two major surfaces comprising, e.g., alumina. Preferred sensors of this type are disclosed in the following United States patent applications: EXHAUST GAS SENSOR (Docket No. 300.002); GAS SENSOR HAVING A POROUS DIFFUSION BARRIER LAYER AND METHOD OF MAKING SAME (Docket No. 300.003); and EXHAUST GAS SENSOR WITH FLOW CONTROL WITHOUT A DIFFUSION BARRIER (Docket No. 300.004), each application being filed of even date herewith and the disclosures of which are hereby expressly incorporated herein by reference. In this case, the catalytic structure is disposed in the exhaust conduit of an internal combustion engine 10, from which engine exhaust is transmitted by exhaust conduit 12 to a catalytic converter 14 which is partially broken away to show a treatment catalyst 16 disposed therein. Treatment catalyst 16 may comprise a monolithic carrier, the gas flow channels of which (not shown) are disposed parallel to the longitudinal axis of exhaust conduit 12. The walls of the gas flow channels are coated with a suitable catalytic material of any known type. The catalytic material utilized in the treatment catalyst may be an oxidation catalyst, such as a platinum-on- alumina support, or it may be the type of catalyst known to those skilled in the art as a three-way conversion catalyst. A three-way conversion catalyst contains a catalytic material which promotes substantially simultaneous oxidation of hydrocarbons and carbon monoxide and reduction of nitrogen oxides. After passing through treatment catalyst 16, the treated exhaust gases pass through a transfer conduit 18, then through a conventional sound-deadening muffler 20, for discharge to the atmosphere via an exhaust pipe 22. The arrangement thus far described is conventional, showing the interposition of a catalytic converter into the exhaust gas discharge of, e.g., an automobile or diesel engine, in order to treat the exhaust gases to reduce the noxious pollutant content thereof prior to discharge to the atmosphere.

Transfer conduit 18 is broken away in FIG. 12 to better show the insertion of a sensor 24 therewithin so that a portion at least of sensor 24 contacts the treated exhaust gases exiting from treatment catalyst 16. Sensor 24 is connected via a first lead 26 to a sensor electronics package 28, which is in turn connected by a second lead 30 to engine control unit 32. Engine control unit 32 is connected by a third lead 34 to engine 10.

Sensor 24 has coated thereon an adherent and cohesive fired coating of catalytic material 24a in accordance with an embodiment of the present invention.

Figure 12A:
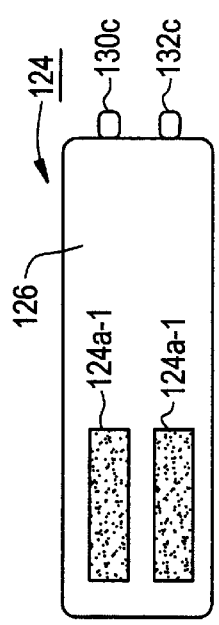
FIGS. 12A and 12B are schematic top and bottom views, respectively, greatly enlarged relative to FIG. 12, of a sensor of the type shown in FIG. 12 with part of the surface layer broken away in FIG. 12B.
Figure 12B:
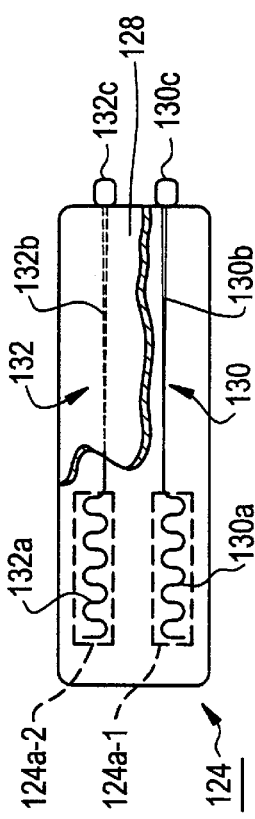

In the known manner, sensor 24 may be heated by, e.g., a platinum electric resistance wire heater which is part of a sensor member which also comprises an electrical resistance thermometer. FIGS. 12A and 12B schematically illustrate a typical catalytic gas sensor 124 of a type usable as the sensor 24 in the system of FIG. 12. Catalytic gas sensor 124 comprises a support member (unnumbered) having a first major surface 126 (FIG. 12A) and an opposite, second major surface 128 (FIG. 12B). The support member is of layered construction with first and second major surfaces 126 and 128 being comprised of alumina. Second major surface 128 is partly broken away in FIG. 12B to show the schematically-illustrated temperature-sensing and electrical heating means embedded within sensor 124 and described below. The support member is thin enough and thermally conductive enough, at least in the area of fired coatings 124a-1 and 124a-2, for heat transfer to take place between the fired coatings 124a-1 and 124a-2 (FIG. 12A) and their associated coil sections 132a, 132b (FIG. 12B). On first major surface 126, there are provided the two fired coatings of catalytic ink, 124a-1 and 124a-2. The first and second major surfaces are major surfaces of a support member made of a ceramic or ceramic-like material such as alumina or silicon nitride. A pair of conductor members 130, 132 are provided on second major surface 128. Conductor member 130 comprises the coil portion 130a which is disposed directly opposite to fired coating 124a-1 which, in FIG. 12B, is shown in dash outline. Conductor member 130 also comprises a connector portion 130b which extends from coil portion 130a to a platinum pad 130c. The construction of conductor member 132 corresponds to that of conductor member 130 and comprises a coil portion 132a, a connector portion 132b and a platinum pad 132c. Fired coating 124a-2 is likewise shown in dash outline in FIG. 12B and is directly opposite coil 132a.

In use, fired coatings 124a-1 and 124a-2 may be heated by current supplied through platinum pads 130c, 132c and conductor members 130, 132 to coil portions 130a, 132a. As reactions are catalyzed at the surfaces of fired coatings 124a-1 and 124a-2, the heat of reaction is sensed by the coil portions 130a, 132a and the temperature increase is sensed by suitable circuitry connected through gold wires to platinum pads 130c and 132c. Thus, conductor members 130, 132 serve both to heat the catalyst and to transmit temperature data showing the additional heating of catalytic fired coatings 124a-1 and 124a-2 by the oxidation (or other) reactions they catalyze. The catalytic compositions on fired coatings 124a-1 and 124a-2 may differ in order to provide data concerning different gases contained in the gas stream being treated by treatment catalyst 16. The temperature increase at fired coating 124a-1, for example, may reflect the amount of hydrocarbon oxidation carried out thereon, and a transducer (not shown) may generate a signal from the increased resistance which signal is transmitted to first lead 26, thence to sensor electronics package 28. This information concerning the amount of hydrocarbon oxidation taking place at catalytic fired coating 124a-1, optionally used in conjunction with other information concerning the conditions in the exhaust stream being treated, indicates the quality of the performance of treatment catalyst 16. That information may be relayed via second lead 30 to engine control unit 32, which transmits an appropriate operating signal via third lead 34 to engine 10, in order to adjust operation thereof. For example, in response to the signal from engine control unit 32, the air/fuel ratio of the fuel supply to the engine may be adjusted in order to enhance performance of treatment catalyst 16. If poor performance persists, catalytic converter 14 may have to be replaced.

EXAMPLE C

Performance Testing of Sensors Catalyzed With Fired Coatings Obtained From Catalytic Inks Alumina sensor bodies of the general type schematically illustrated in FIGS. 12A and 12B and containing two platinum resistance thermometers were provided by Motorola, Inc., along with suitable electronics packages, for continually determining resistance measurements of the thermometers. The thermometer resistance is proportional to the temperature of the thermometers. Catalyst is deposited on the sensor by screen printing a catalytic ink immediately adjacent or over the resistance thermometers, or one of them, in accordance with the practices of the present invention. For test purposes, the catalytic ink was deposited on a thin alumina layer, on the underside of which the thermometer and the circuitry of the sensor are located. Thus, a thin layer of alumina supports the thermometer and its associated circuitry. This is as illustrated in FIGS. 12A and 12B, wherein coiled portions 130a and 132a and associated circuitry (not shown in FIGS. 12A and 12B) are located on second major surface 128 of gas sensor 124 so that first major surface 126 thereof provides a thin layer of the substrate (alumina in the case of the tested sensors) on which a fired coating such as fired coating 124a-1, shown in FIG. 12A, is deposited. In the present case, only one such fired coating is applied and the other resistance thermometer is left bare (uncatalyzed). Thus, with reference to FIGS. 12A and 12B, the tested structure has a fired coating equivalent to 124a-1 but the fired coating equivalent to 124a-2 was omitted. Therefore, when the sensor is exposed to a combustible gas at an appropriate temperature in the presence of an oxidizing agent such as air or oxygen, a change in resistance on a catalyzed thermometer will be indicative of heat liberated by combustion of a reactant on the catalyst. The electronic signal from the blank thermometer channel is subtracted from the catalyzed thermometer channel to eliminate systematic error due to flow changes, temperature drift, etc.

Preparation of Catalytic Inks For Screen Printing

Zirconium resinate, calcium resinate, bismuth resinate and rare earth metal resinate were all purchased from Mooney Chemicals, Franklin, Pa. or the OM Group of Mooney Chemicals, Cleveland, Ohio, under the respective trademarks or designations *Zr Chem All Synthetic, Ca Chem All Synthetic, Bi Catalyst* 320 and *Rare Earth TEN-CEM,* A3965, respectively. These materials comprise the metal salts of 2-ethylhexanoic acid, plus a mineral spirits carrier.

Silicon resinate, a silicon salt of 2-ethylhexanoic acid, and rhodium resinate, a rhodium salt of trimethylcyclohexanoate, were manufactured by Engelhard Corporation at East Newark, N.J.

The catalyst used in preparing the catalytic inks used in Examples 12–17 were of two types. The first type is a "total combustibles catalyst" (Examples 12, 13, 15 and 16) which is selected to have a high loading of highly active catalytic metal so as to assure substantially total oxidation of all oxidizeable components in the stream being treated or tested when oxidizing conditions are maintained. Such a total combustibles catalyst would typically comprise one or more of platinum, rhodium, palladium, iridium and ruthenium, preferably, one or more of platinum, rhodium and palladium, for example, platinum plus rhodium. As described elsewhere herein, these catalytic metal components would be dispersed upon a stable refractory metal oxide support, such as alumina, zirconia, titania, silica, silica-alumina, etc., in powder form. As also described elsewhere herein, thermally stabilized materials, whether stabilized by thermal, hydrothermal or chemical means, such as precalcined alumina, ceria-stabilized alumina, ceria-stabilized zirconia, alumina-stabilized ceria, etc., are preferred for the support materials. The function of the total combustibles catalyst is to convert, i.e., oxidize, all combustibles such as hydrogen, carbon monoxide and hydrocarbons in the stream being tested or treated.

The second catalyst type (Examples 14 and 17) is a catalyst which selectively promotes the oxidation of carbon monoxide in the presence of hydrocarbons. Such "carbon monoxide selective catalyst" functions to promote the oxidation of carbon monoxide to carbon dioxide (and the oxidation of hydrogen to $H_2O$) with no or very little oxidation of hydrocarbons, e.g., olefins, contained in the stream being tested or treated under oxidizing conditions. One such carbon monoxide selective catalyst is disclosed in commonly assigned co-pending patent application Ser. No. 08/887,483, filed on Jul. 2, 1997, in the name of Gerald S. Koermer et al for "Catalyst For Selective Oxidation of Carbon Monoxide and Method Using the Same". The disclosure of that application is hereby incorporated herein and essentially shows a selective catalytic material for selectively oxidizing carbon monoxide in a gas stream containing a hydrocarbon component in addition to the carbon monoxide. The catalytic material comprises a catalytically effective amount of rhodium and a bismuth component which is present in an amount sufficient to inhibit the oxidation of the hydrocarbon component when the selective catalytic material is contacted under oxidizing conditions with the gas stream. Thus, the catalyst may comprise the usual refractory inorganic oxide support, a catalytically effective amount of rhodium dispersed on the support and a bismuth component, for example, $Bi_2O_3$, dispersed on the support in an amount sufficient to inhibit the oxidation of the hydrocarbon component when the selective catalytic material is contacted under oxidizing conditions with the gas stream. The catalytic metal component may comprise one or more platinum group metals other than rhodium, for example, platinum, which will catalyze the oxidation of carbon monoxide to carbon dioxide but its catalytic effect for the oxidation of hydrocarbons is inhibited by the presence of the bismuth component.

EXAMPLE 12

A Catalytic Ink I was prepared using the following recipe. Sixty grams of Catalyst A of Example 1, a total combustibles catalyst, was prepared. The catalyst was mixed with 10 grams of zirconium resinate, 10 grams of calcium resinate and 5 grams of silicon resinate. Fifteen grams of an ethyl cellulose vehicle in taxanol was added to adjust the viscosity of the mixture for screen printing. The mixture was passed through a three roll mill continually until it became homogeneous. The resulting Catalytic Ink I was screen printed onto the sensor as described above in connection with FIGS. 12A and 12B, so that the Catalytic Ink I overlays one resistance thermometer thereof (as illustrated in FIGS. 12A and 12B), but not the other. The sensor was dried in an oven at about 125° C. for approximately 15 minutes and then fired in a belt furnace whose peak temperature was 850° C. The peak temperature was sustained for 10 minutes and the total firing time in the belt furnace was approximately 45 minutes.

EXAMPLE 13

A Catalytic Ink II was prepared using the following recipe. Fifty-three grams of Catalyst B of Example 4, a total combustibles catalyst, was prepared. The catalyst was mixed with 13.24 grams of zirconium resinate, 8.82 grams of rare earth resinate and 24.94 grams of the ethyl cellulose vehicle used in Example 12. The mixture was passed through a three roll mill continually until it became homogeneous. The resulting Catalytic Ink II was screen printed onto the sensor as described in Example 12 so that the ink overlaid one resistance thermometer (as illustrated in FIGS. 12A and 12B) but not the other. The sensor was dried in an oven at about 125° C. for approximately 15 minutes and then fired in a belt furnace whose peak temperature was 850° C. The peak temperature was sustained for 10 minutes and the total firing time in the belt furnace was approximately 45 minutes.

EXAMPLE 14

A Catalytic Ink III was prepared as follows. Fifty-five grams of ceria-stabilized zirconia was combined with 19.3 grams of bismuth resinate, 12.7 grams of rhodium resinate and 13.0 grams of the ethyl cellulose vehicle of Example 12. The mixture was passed through a three roll mill continually until it became homogeneous. The resulting Catalytic Ink III was screen printed onto the sensor as described in Example 12 so that the ink overlaid one resistance thermometer (as illustrated in FIGS. 12A and 12B) but not the other. The sensor was dried in an oven at about 125° C. for approximately 15 minutes and then fired in a belt furnace whose peak temperature was 850° C. The peak temperature was sustained for 10 minutes and the total firing time in the belt furnace was approximately 45 minutes. In this case, the resinate has two functions. In the first function, the resinates combine with the ceria-zirconia to form a catalyst that, because of the bismuth content, selectively oxidizes carbon monoxide in the presence of hydrocarbons, in the manner as described above with respect to co-pending patent application Ser. No.08/887,483. The second function of the resinates is to bind the catalyst particles to the sensor body.

EXAMPLE 15

Figure 13:
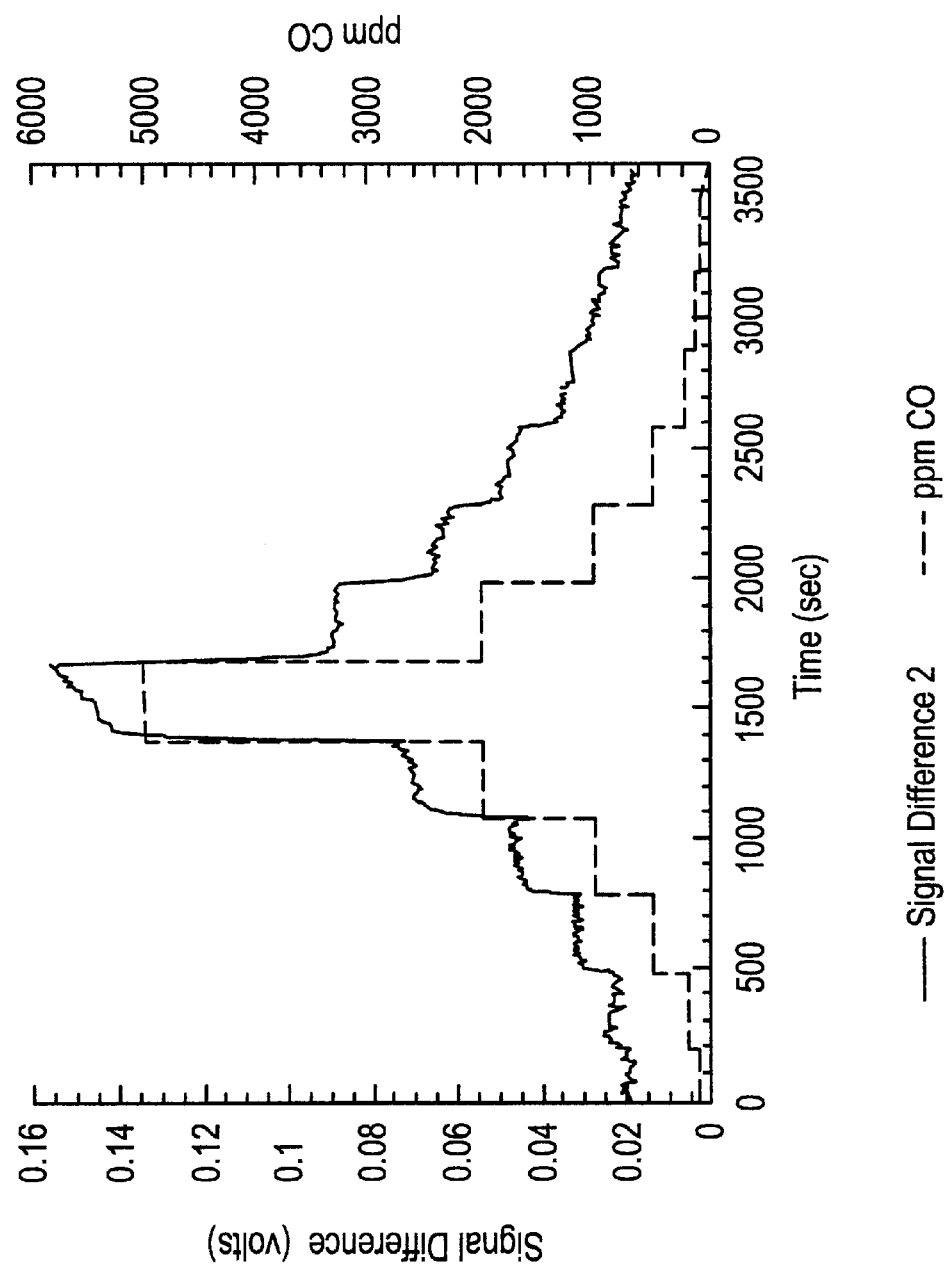
FIGS. 13, 14 and 15 are graphs showing the difference in signals generated by the two platinum wire thermometers of a sensor disposed in a gas stream and containing oxidizable components under oxidizing conditions, one of the thermometers being overlain by a fired coating of catalytic ink, and the other not.
Figure 14:
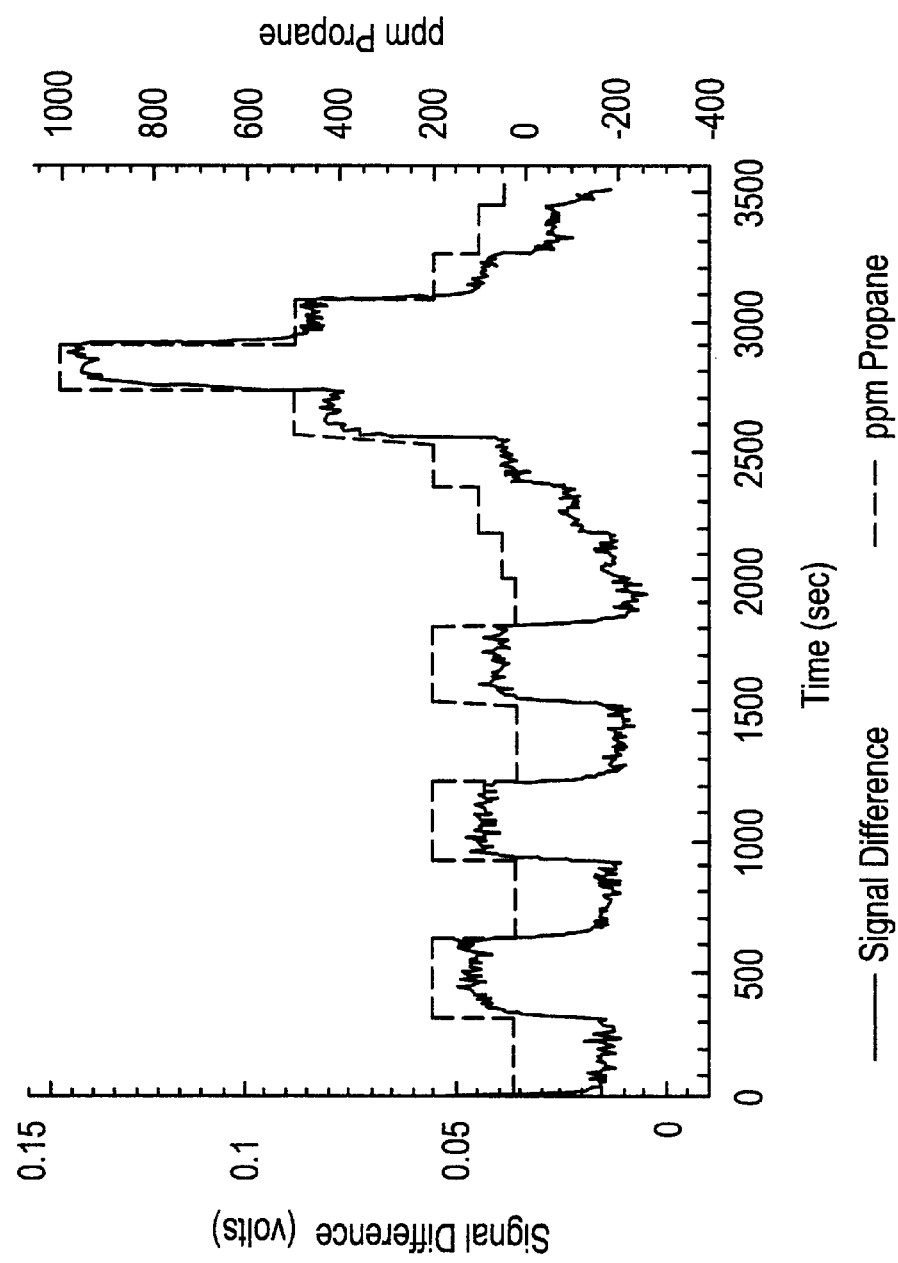
Figure 15:
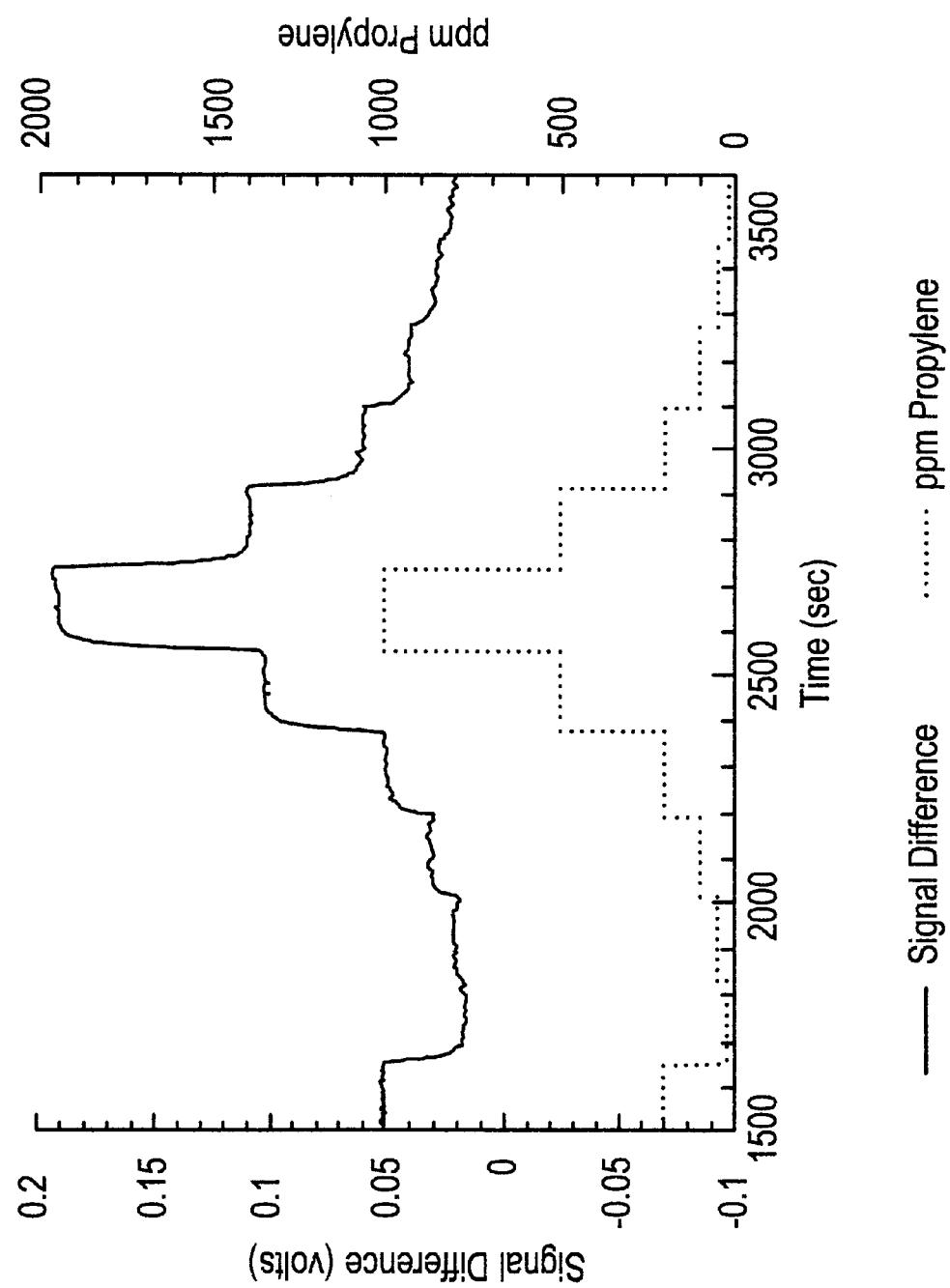

The performance of the sensor made using Catalytic Ink I is shown in FIGS. 13 to 15. The data were obtained at 400° C. FIG. 13 shows the difference in the signal (in volts) generated by the two thermometers in a gas stream in which carbon monoxide was the only oxidizable constituent present. It is seen that over a timespan of 3,500 seconds, a clearly discernible difference, on the order of about 0.02 volts, was maintained in the two different signals. FIG. 14 shows a similar set of data when propane is the oxidizable constituent. Here too, a discernible difference is maintained between the strength of the signals in volts generated by the catalyzed and uncatalyzed platinum wire thermometers.

FIG. 15 shows a signal difference in volts when propylene is the oxidizable constituent. A clear response of the sensor to concentrations of carbon monoxide, propane and propene is observed.

EXAMPLE 16

The performance of the sensor made with Catalytic Ink II showed results similar to those illustrated in FIGS. 13 to 15 in that a clearly discernible signal difference between the catalyzed and uncatalyzed thermometers was noted. Thus, a clear response of the sensor to concentrations of carbon monoxide, propane and propene was observed.

EXAMPLE 17

The performance of the sensor made with Catalytic Ink III showed a discernible signal difference between the catalyzed and uncatalyzed thermometer for carbon monoxide, but very little or no difference in the signals in the cases where propane and propene were the oxidizable components. Thus, a clear response of the sensor to carbon monoxide was observed but little or no response to propane and propene was observed. This showed that the catalyst of Catalytic Ink II is very highly selective for oxidation of carbon monoxide and that it retained this selectivity while being bound to the sensor body.

While the invention has been described in detail with respect to specific preferred embodiments thereof, it is to be understood that upon a reading of the foregoing description, variations to the specific embodiments disclosed may occur to those skilled in the art and it is intended to include such variations within the scope of the appended claims.

What is claimed is:

1. A catalytic structure comprising a support member on which is disposed a catalytic material comprising a fired coating of a catalytic ink, the catalytic ink being comprised of a liquid vehicle, at least one metal resinate compound comprising a metal moiety and an organic moiety, and having therein a catalytically effective amount of a catalytic metal component, the metal moiety being characterized by comprising at least one metal which forms in the fired coating an inorganic network which adheres the catalytic metal component to the substrate in a coherent layer.

2. The catalytic structure of claim 1 wherein the metal moiety of the metal resinate comprises at least a part of the catalytic metal component.

3. The catalytic structure of claim 1 or claim 2 wherein the catalytic ink further comprises fine particles of a refractory metal oxide.

4. The catalytic structure of claim 3 wherein at least a part of the catalytic metal component in the catalytic ink is derived from a source other than the metal resinate and is dispersed on the particles of refractory metal oxide.

5. The catalytic structure of claim 1 wherein the metal moiety is selected from the group consisting of one or more of bismuth, calcium, rare earth metal, tin and zirconium.

6. A catalytic structure comprising a support member on which is disposed a catalytic material comprising a fired coating of a catalytic ink, the catalytic ink being comprised of a liquid vehicle, at least one metal resinate compound, and a catalytically effective amount of a catalytic metal component, the metal moiety comprising a first metal moiety characterized by forming in the fired coating an inorganic network which adheres the catalytic metal component to the substrate in a coherent layer, and a second metal moiety which comprises the catalytic metal component.

7. The catalytic structure of claim 1, claim 2 or claim 6 wherein the support member comprises a ceramic material, the vehicle is an organic solvent and the metal resinate compound is selected from the group consisting of one or more of bismuth, calcium, chromium, cobalt, copper, iron, lead, lithium, manganese, nickel, palladium, platinum, potassium, rare earth metal, rhodium, silicon, silver, tin, zinc and zirconium resinates.

8. The catalytic structure of claim 1, claim 2 or claim 6 wherein the metal resinate compound is selected from the group consisting of one or more of bismuth, rhodium, rare earth metal and zirconium resinates.

9. The catalytic structure of claim 1, claim 2 or claim 6 wherein the metal of the catalytic metal component is selected from the group consisting of one or more platinum group metal components.

10. The catalytic structure of claim 9 wherein the one or more platinum group metal components are present in the amount of at least about 30 mg/m² of the fired coating.

11. The catalytic structure of claim 1, claim 2 or claim 6 comprising a catalytic gas sensor wherein there is disposed on the support member in heat transfer relationship with the coating of catalytic ink at least one conductor member comprising temperature sensing means and electrical heating means.

12. The catalytic structure of claim 11 wherein the support member has first and second opposite major surfaces and the catalytic material is on the first surface and the conductor member is embedded within the sensor.

13. The catalytic structure of claim 6 wherein the first metal moiety is selected from the group consisting of one or more of bismuth, calcium, rare earth metal, tin and zirconium, and the second metal moiety is selected from the group consisting of chromium, cobalt, copper, iron, manganese, nickel, palladium, platinum, rhodium and silver.

14. The catalytic structure of claim 6 further comprising fine particles of a refractory metal oxide having dispersed thereon at least some of the catalytic metal component.

15. The catalytic structure of claim 1, claim 2 or claim 14 wherein the particles have a mean diameter of not greater than about 20 microns and a size distribution such that at least 50 percent of the particles have a mean diameter of not greater than about 10 microns and at least about 25 percent of the particles have a mean diameter of not greater than about 5 microns.

16. The catalytic structure of claim 15 wherein the catalytic metal component is present in the amount of from about 30 to 9000 mg/m² of the fired coating.

17. A catalytic gas sensor comprising:
(a) a support member made of a thermally conductive and electrically insulative material and having a first major surface and a second, opposite major surface;

(b) a catalytic material comprising a fired coating of a catalytic ink, the catalytic ink being comprised of a liquid vehicle, at least one metal resinate compound having a metal moiety and an organic moiety, the metal moiety being characterized by comprising at least one metal which forms in the fired coating an inorganic network which adheres the catalytic metal component to the substrate in a coherent layer, and a catalytically effective amount of a catalytic metal component present in the fired coating in the amount of at least about 30 mg/m² calculated as the elemental metal;
(c) temperature-sensing means disposed in heat-transfer relationship with the catalytic material; and
(d) electrical heating means disposed in heat-transfer relationship with the catalytic material.

18. The sensor of claim 17 wherein the catalytic metal component comprises at least one platinum group metal component.

19. The sensor of claim 17 or claim 18 wherein the metal moiety of the metal resinate comprises at least a part of the catalytic metal component.

20. The sensor of claim 19 or claim 18 wherein the catalytic ink further comprises fine particles of a refractory metal oxide.

21. The sensor of claim 20 wherein at least a part of the catalytic metal component in the catalytic ink is dispersed on the particles of refractory metal oxide independently of the metal resinate.

22. The sensor of claim 17 or claim 18 wherein the catalytic ink is further comprised of fine particles of a refractory metal oxide having dispersed thereon a catalytically effective amount of the catalytic metal component.

23. The sensor of claim 17 wherein the fired coating is disposed on the first major surface and both the temperature-sensing means and the electrical heating means are disposed on the second major surface whereby heat transfer between the catalytic material and each of the temperature-sensing means and the electrical heating means is through the support member.

24. The sensor of claim 23 wherein at least one of each of the temperature-sensing means is disposed directly opposite the catalytic material.

25. The gas sensor of claim 17 wherein the metal moiety is selected from the group consisting of one or more of bismuth, calcium, rare earth metal, tin and zirconium.

* * * * *